United States Patent [19]

Blom et al.

[11] Patent Number: 4,614,516

[45] Date of Patent: * Sep. 30, 1986

[54] VOICE PROSTHESIS DEVICE

[75] Inventors: Eric D. Blom, Indianapolis; Mark I. Singer, Carmel, both of Ind.

[73] Assignee: Hansa Medical Products, Inc., Indianapolis, Ind.

[*] Notice: The portion of the term of this patent subsequent to Mar. 13, 2001 has been disclaimed.

[21] Appl. No.: 572,249

[22] Filed: Jan. 20, 1984

Related U.S. Application Data

[63] Continuation-in-part of Ser. No. 373,635, Apr. 30, 1982, Pat. No. 4,435,853.

[51] Int. Cl.$^4$ .............................................. A61F 2/20
[52] U.S. Cl. ...................................................... 623/9
[58] Field of Search ............................ 3/1.3; 128/136; 137/855

[56] References Cited

U.S. PATENT DOCUMENTS 155,667 10/1874 Painter ................................. 137/855
4,435,853 3/1984 Blom et al. ............................ 3/1.3
4,475,888 10/1984 Gores et al. ......................... 128/136

Primary Examiner—Richard J. Apley
Assistant Examiner—James Prizant
Attorney, Agent, or Firm—Barnes & Thornburg

[57] ABSTRACT

A low pressure prosthesis device includes a housing having a proximal end with one or more retainers extending outwardly from the proximal end, a distal end and a port operatively cooperating with a tracheostoma in the neck of a patient. The housing further includes a one-way valve structure comprising a valve seat positioned in the housing between the port and the distal end and a valve membrane hingedly mounted within the housing to cooperate with the valve seat to provide the one-way valve structure. A second retainer in the form of an annular collar extends outwardly from the housing and is positioned to abut against the esophagus tissue when the device has been positioned within a fistula connecting the esophagus to the tracheostoma. The valve membrane is movable from the closed to the opened position when air passes through the port from the tracheostoma to the esophagus to produce alaryngeal speech and sounds in the patient.

17 Claims, 9 Drawing Figures

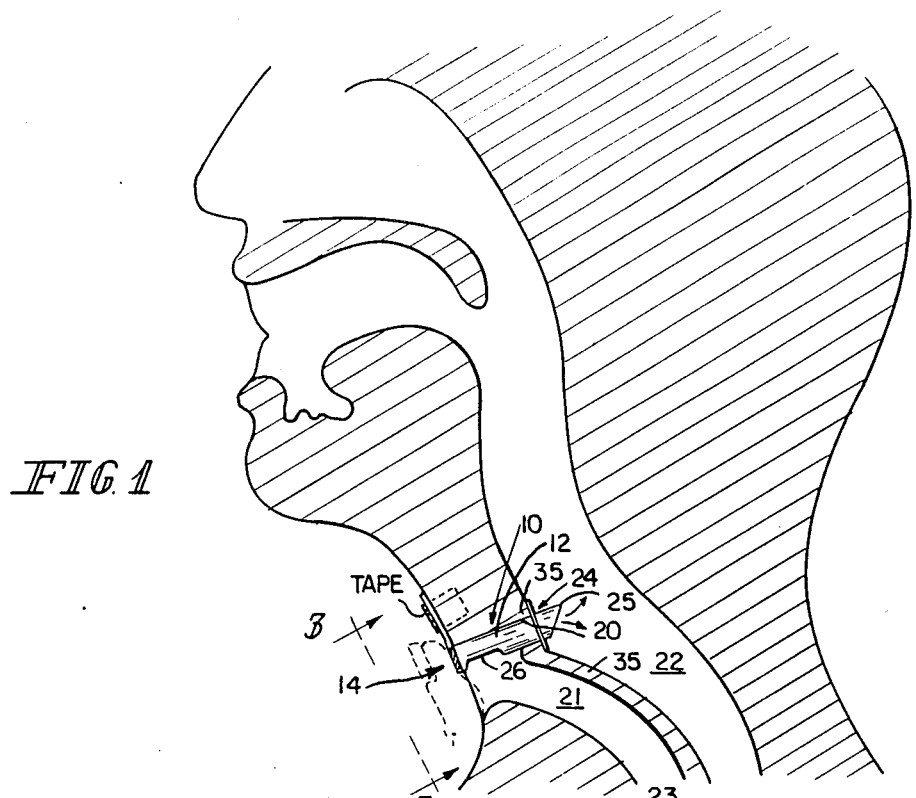
FIG. 1
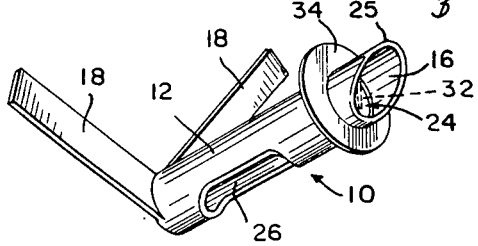
FIG. 2
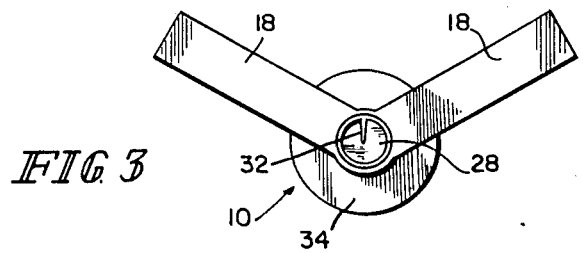
FIG. 3
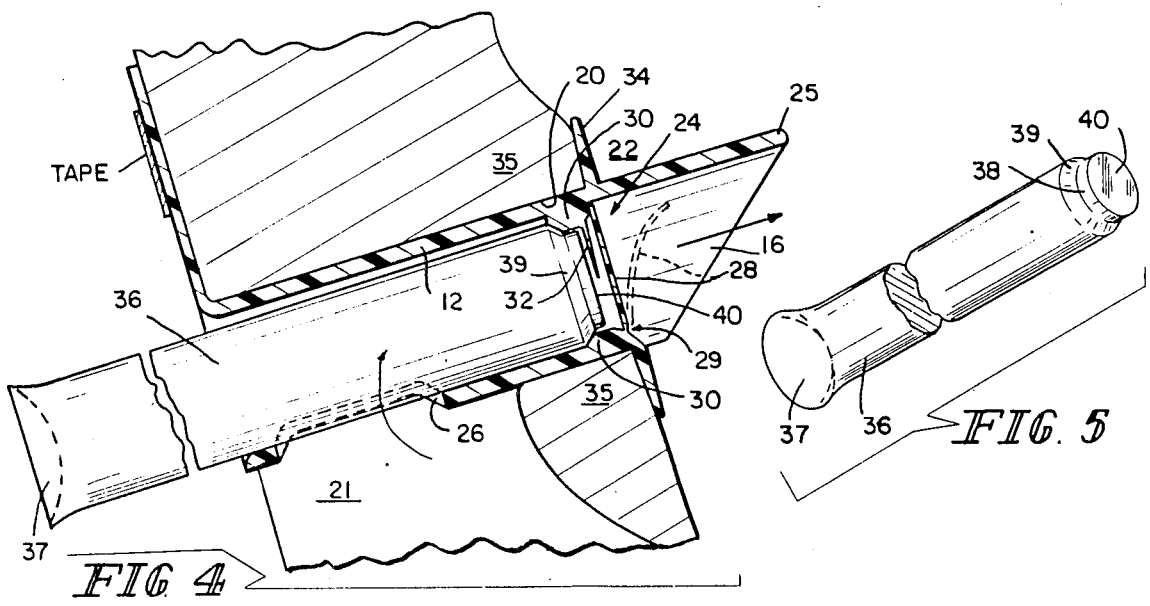
FIG. 4
FIG. 5

VOICE PROSTHESIS DEVICE

This is a continuation-in-part of our earlier filed co-pending U.S. patent application Ser. No. 373,635, filed on Apr. 30, 1982, now U.S. Pat. No. 4,435,853.

The present invention relates to a novel voice prosthesis device which is insertable through a fistula to connect and channel air directly from the lungs through the trachea to the esophagus for voice restoration after a total laryngectomy.

In the past, voice prosthesis devices have been suggested for insertion into a fistula to connect the tracheostoma with the esophagus to channel air from the lungs to the esophagus to permit alaryngeal speech by the patient or user. One such voice prosthesis device is disclosed, in our co-pending application Ser. No. 316,055, filed on Oct. 29, 1981, and entitled "Method and Apparatus for a Tracheal Valve", and in a paper entitled "An Endoscopic Technique for Restoration of Voice After Laryngectomy", *Annals of Otology, Rhinology and Laryngology*, 1980, Vol. 89, No. 6. However, the elongated hollow tube or duck-bill type valve slit in the elongated hollow tube requires approximately 90 centimeters of water pressure before the duck-bill type valve opens to permit air to enter the esophagus for speaking. Additionally, a voice prosthesis device, known as the Panje device, is a shorted criss-crossed slitted duck-bill device, which includes self-retaining flanges which abut against each side of the tracheoesophageal wall to hold the device in the fistula. However, the Panje type device requires approximately 400 centimeters of water pressure before voice sounds are achieved, a pressure which is totally unsatisfactory for most, if not all, patients or users. Because a normal larynx requires approximately 35 centimeters of water pressure for speech, it can be seen that a voice prosthesis device, which closely approximates normal voice pressure, is highly desirable and has been unattained by the duck-bill type prior art devices.

Additionally, U.S. Pat. No. 3,747,127 discloses a fistula valve FA which is merely a check valve mounted on the outside of the exterior proximal end of a tubular extension. Because the valve opens and closes from the top of the proximal end and is unprotected because it is not in a recessed position within the tube, such a structure is unsatisfactory in communicating between the trachea and the esophagus because the valve is readily exposed to the esophageal contents, and liquids and matter therein may penetrate the valve from the esophagus with resultant aspiration into the lungs of the user or patient. Also, because the valve is unprotected, its operation can be affected by the surrounding tissue. Accordingly, such devices have found no application in restoring speech to patients having a total laryngectomy.

It is an object of the present invention to provide a low-pressure voice prosthesis device which includes valve means positioned therein which approximates the valvular resistance to air flow presented by the larynx.

It is another object of the present invention to provide a voice prosthesis device with a low-pressure valvular design that is internalized in the distal end of the prosthesis device to protect the valve opening and closing excursion from becoming impeded by tissue or esophageal contents.

It is a further object of the present invention to provide novel voice prosthesis device which is reliable in operation and which is a minature one-way valved tube readily positioned in a patient having a total laryngectomy and subsequent tracheoesophageal fistula.

It is still another object of the present invention to provide a novel tool structure for positioning the low-pressure voice prosthesis device into the prescribed position in a patient.

The voice prosthesis device in accordance with the present invention is useful when inserted into a fistula to direct or channel pulmonary air from the tracheostoma into the esophagus of a patient to produce alaryngeal speech. The voice prosthesis device includes an elongated tubular housing which is constructed and composed of a biocompatible material or a combination of biocompatible materials. An example of such materials is a medical grade silicone material. The voice prosthesis device has a proximal or tracheal end and a distal or esophageal end. Attached to the proximal end is a flange means or strap means comprising one or more strap-like projections which extend generally radially away from the axis of the housing which aids and assists as retention means in maintaining the voice prosthesis device in the fistula between the tracheostoma and esophagus. A one-way valve is positioned intermediate the proximal and distal ends of the housing, as will hereinafter be described. The elongated tubular housing includes a hood formed on the distal end thereof which extends into the esophagus to guard against exposure of the one-way valve to material in the esophagus.

The housing includes a port therein which permits expelled air from the tracheostoma to enter the voice prosthesis device and pass through the one-way valve into the esophagus to produce alaryngeal speech in the patient. The one-way valve structure, positioned within the voice prosthesis device, is comprised of a valve membrane hinged on the interior of the housing and adjacent to a valve seat or sealing structure provided within the housing to provide a hinged valve which permits the passage of air from the trachea into the esophagus. It is preferred that the valve membrane be mounted and hinged on the inferior or lower portion or side of the housing and that the valve structure be opened and closed by a pressure comparable to the pressure necessary to operate a normal larynx, or approximately about 35 centimeters of water pressure.

Additionally, the housing of the prosthesis device includes a retention collar provided on its outside surface between the port and the distal end of the housing. The retention collar structure aids in obtaining a seal when the voice prosthesis device is inserted through the fistula and abuts the esophageal surfaces of the tracheoesophageal wall to retain and hold the voice prosthesis device in position.

The novel voice prosthesis device structure in accordance with the present invention provides a low-pressure voice prosthesis device whose operative pressure closely approximates the pressure necessary to operate a normal individual's larnyx. Such a reduction in pressure necessary to move the one-way valve from the closed to the open position greatly reduces the strain upon the patient in producing alaryngeal speech and permits the patient to produce alaryngeal speech and sounds similar to those produced by the patient's former larynx. Moreover, it has been found that when the one-way valve membrane is in the closed position, during normal swallowing, the positive pressure gradient within the esophagus further seats the valve membrane to its closed position to enhance its effectiveness as a one-way valve. Additionally, the hood on the distal end of the cylindrical housing acts to shelter the valve from fluid and other matter that is swallowed through the esophagus. This permits an increased wearing time by the patient of the novel voice prosthesis device in accordance with the present invention. Also, the retention collar provides a locking action when the retention collar is inserted through the fistula to abut against the esophageal side of the tracheoesophageal wall to hold and retain the novel prosthesis device in position. This locking action provided by the retention collar, together with the flange, strap or other retention means on the proximal end of the cylindrical housing, reduces the likelihood of the device becoming dislodged during usage by a patient.

FIG. 1 is a schematic view showing the installation in a patient of the voice prosthesis device in accordance with the present invention;

FIG. 2 is a perspective view of the voice prosthesis device in accordance with the present invention;

FIG. 3 is an end view taken along lines 3—3 of FIG. 1;

FIG. 4 is an enlarged view showing the passage of air through the one-way valve structure of a voice prosthesis device in accordance with the present invention;

FIG. 5 is a perspective view of the placement tool for positioning the voice prosthesis device in accordance with the present invention in a patient;

Figure 6:
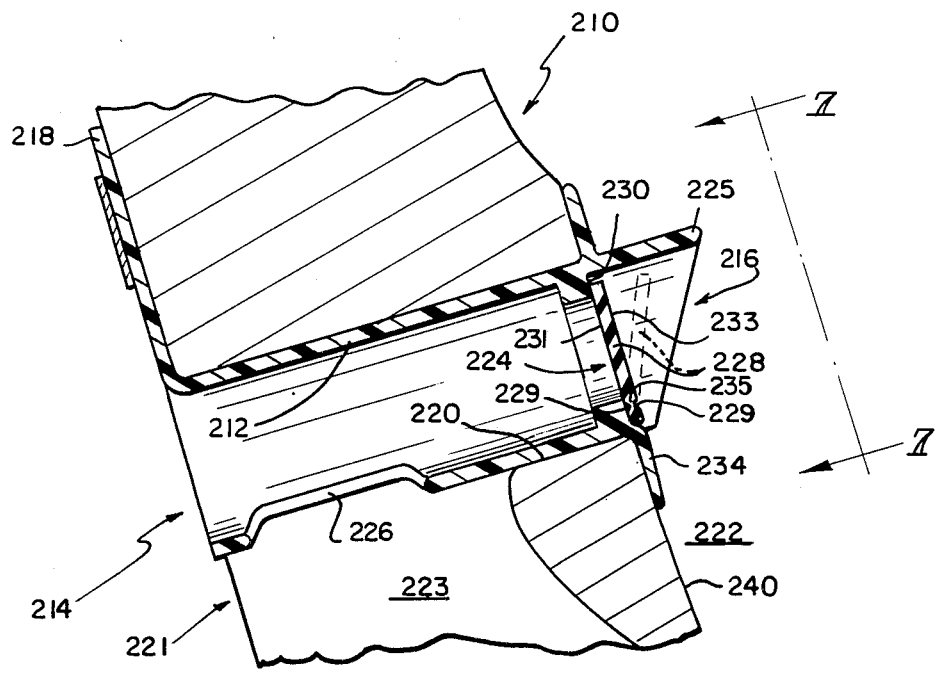
FIG. 6 illustrates a longitudinal sectional view through another one-way valve structure constructed according to the present invention.

Referring now to FIGS. 1-5 wherein like numerals have been used to designate the same or similar parts, FIG. 1 shows the voice prosthesis device 10 in accordance with the present invention positioned in a patient having a total laryngectomy.

As shown in FIGS. 2-4, the voice prosthesis device 10 includes an elongated tubular housing 12 which is constructed and composed of a medical grade silicone material having a proximal or tracheal end 14 and a distal or esophageal end 16. Although the housing 12 has been illustrated as being right circular cylindrical in cross section, other cross sectional shapes, such as right elliptical cylindrical, can be employed. Mounted to the proximal end 14 are retention means in the form of upwardly inclined, angularly separated straps 18 (FIGS. 2 and 3) which may be taped to the neck of the patient (FIG. 1) to assist in retaining and maintaining the voice prosthesis device 10 in a fistula 20, which is a surgical connection between the tracheostoma 21 and the esophagus 22 of the patient. The elongated tubular housing 12 includes a protective hood in the form of a beveled extension member 25 on the distal end 16 which extends into the esophagus 22. The hood 25 shields the end of the housing 12 against the influx of material flowing down the esophagus. A one-way valve 24 is positioned within and adjacent the distal end 16 of the cylindrical housing, as will hereinafter be described.

The cylindrical housing 12 includes also a port 26 positioned between the proximal end 14 and the one-way valve 24. Port 26 permits expelled air from the tracheostoma 21 and the trachea 23 to enter the tubular housing 12 of the voice prosthesis device and pass through the one-way valve 24 into the esophagus 22 to produce alaryngeal speech in the patient.

The one-way valve 24 is positioned within the tubular housing and includes a valve membrane 28 (FIG. 4) hinged 29 on the interior of the cylindrical housing and adjacent to a valve seat 30 (FIG. 4) provided within the cylindrical housing 12. The valve seat 30, which is in the form of an annular seal, cooperates with the hinged valve membrane 28 to permit the passage or channeling of air from the trachea 23 into the esophagus 22, as will hereinafter be described, but to block the flow of material from the esophagus 22 into the trachea 23. It is preferred that the valve membrane 28 be mounted and hinged 29 on the interior side of the valve membrane 28 on the bottom thereof and that the valve membrane be opened and closed by a pressure comparable to that necessary to operate a normal larynx, or approximately 35 centimeters of water pressure. Also, it is preferred that a projection 32 (FIG. 4) extend downwardly from the interior of the housing 12 toward the center of the cylindrical housing, which projection 32 reduces the possibility that the pressure-sensitive valve membrane 28 can overlap the valve seat 30 due to back pressure when the voice prosthesis device 10 is operating or inadvertently during cleaning of the prosthesis device 10.

The cylindrical housing 12 further includes a retention collar 34 in the form of an annular flange. The retention collar 34 is positioned between the distal end of the housing 12 and the port 26. The retention collar 34 aids in maintaining the position of the device 10 in the fistula and in obtaining a seal when the voice prosthesis device is inserted through the fistula because the retention collar abuts and engages the esophageal side of the tracheoesophageal wall 35 to retain and hold the prosthesis device in position. During insertion of the device through a fistula, it has been observed that the retention collar snaps into position against the esophageal tissues when the device has been properly positioned in the patient. When in such a position, the device is firmly retained in position and is not likely to become dislodged.

In FIG. 5, a placement tool 36 is shown which is particularly useful in engaging the voice prosthesis device 10 when the device is positioned through the fistula 20 to connect the esophagus and the tracheostoma. The placement tool 36 preferably includes an enlarged gripping or handle end 37 adapted to receive a finger or thumb of the patient and a placement end 38. The placement end 38 includes a projection 40 thereon, the shoulder 39 of which is adapted to cooperate with and engage the valve seat 30, as will hereinafter be described. When the placement tool is inserted into the elongated tubular housing 12, the shoulder 39 on the placement end 38 engages the valve seat 30 to position the device in the fistula to connect the esophagus and trachea. However, the projection 40 does not engage or disturb the sensitive valve membrane 28 of the one-way valve means 24 during this operation, as shown in FIG. 4. Thus, during insertion of the voice prosthesis device into the fistula, the patient is insured that the valve membrane 28 will be in aligned relation with respect to the annular sealing structure 30 and will be in operative condition.

It is preferred that a projection 32 extend inwardly from adjacent the valve seat 30 towards the center of the passageway through the housing 12. The projection 32 reduces the possibility that the valve membrane 28 can overlap the valve seat 30 during usage of the prosthesis device, cleaning, and placement of the device into the fistula connecting the esophagus and the tracheostoma. During placement, the tendency of voice prosthesis devices is to collapse and be squeezed together and, accordingly, the projection 32 helps to prevent the valve membrane 28 from overlapping the annular sealing rim and becoming inoperative. To prevent the squeezing of the valve means 24 during insertion, the placement tool 36, when positioned within the distal end 14 of the tubular housing 12, insures that the one-way valve means 24 is maintained in proper aligned position to provide the unique low-pressure operation of the voice prosthesis device.

The voice prosthesis device and one-way valve means mounted therein in accordance with the embodiment of FIGS. 1-5 provides a low-pressure voice prosthesis device whose operative pressure closely approximates the pressure required to operate the normal larynx of an individual and has particular application and use in conjunction with the tracheal valve disclosed in our co-pending application Ser. No. 316,055. It has been observed that the average pressure necessary to operate a normal larynx is about 35 centimeters of water and initial observation of the present invention indicates that a range of about that pressure or less readily moves the valve membrane from the closed to the open position. Such a reduction in the pressure necessary to move the one-way valve membrane from the closed to the open position greatly reduces the strain upon the patient in producing alaryngeal speech and sounds similar to those produced by the patient's former larynx. Alaryngeal speech occurs when a finger (as shown in dotted lines) covers the opening to the tracheostoma 21 and air is directed through port 26 and into the esophagus 22. Additionally, as shown in FIG. 4, it has been found that when the one-way valve membrane is in the closed position, normal swallowing by the patient will further seat the valve membrane to insure an effective one-way valve in the closed position.

Also, the positioning of the one-way valve means 24 at or adjacent the distal end 16 of the housing 12 and the cooperation with the hood 25 thereon protects the valve membrane during its opening and closing excursion or movement from esophageal fluids and other matter. The hood 25 also acts as a shield which deflects esophageal fluids or swallowed matter around the housing 12 and thus prevents the downward flow of such swallowed matter from becoming impeded.

Figure 7:
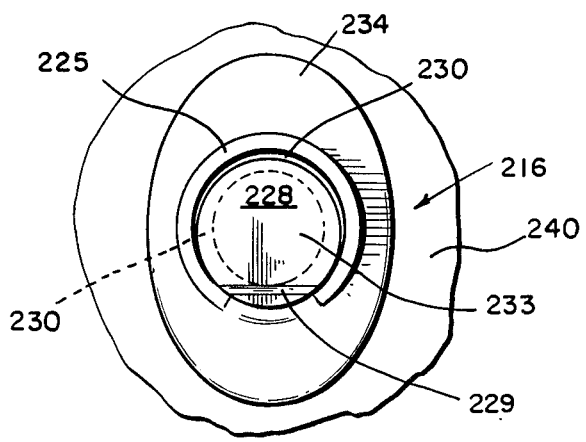
FIG. 7 illustrates an end view of the device of FIG. 6, taken generally along section lines 7—7 thereof.

FIGS. 6-7 show another embodiment of the voice prosthesis device 210 in accordance with the present invention positioned in a patient having a total laryngectomy. The voice prosthesis device 210 includes an elongated tubular housing 212 which again is constructed and composed of a biocompatible material having a proximal or tracheal end 214 and a distal or esophageal end 216. Although the housing 212 has been illustrated as being right circular cylindrical in cross section, other cross sectional shapes, such as right elliptical cylindrical, can be employed. Mounted to the proximal end 214 is a retention means in the form of a single generally vertically upwardly projecting tab 218 which is taped to the neck of the patient to assist in retaining and maintaining the voice prosthesis device 210 in a fistula 220. The elongated tubular housing 212 includes a protective hood 225 on the distal end 216 which extends into the esophagus 222 of the wearer. The hood 225 shields the distal end 216 of the housing 212 against the influx of material flowing down the esophagus 222. A one-way valve 224 is positioned within and adjacent the distal end 216 of the cylindrical housing.

The cylindrical housing 212 includes also a port 226 positioned between the proximal end 214 and the one-way valve 224. Port 226 permits expelled air from the tracheostoma 221 and the trachea 223 to enter the tubular housing 212 of the voice prosthesis device and pass through the one-way valve 224 into the esophagus 222 to produce alaryngeal speech in the patient.

The one-way valve 224 is positioned within the tubular housing and includes a circular valve disk 228 scored at 229 on both sides 231, 233 along a chord of the circle defined by the disk 228. The score lines 229 extend to a depth such that a very flexible region 235 of the disk 228 material remains between them. A valve seat 230, which is in the form of a rectangular cross section annular seal, cooperates with the valve disk 228 to permit the passage or channeling of air from the trachea 223 into the esophagus 222, but to block the flow of material from the esophagus 222 into the trachea 223. It is preferred that the valve disk 228 hinged by the chordal score lines 229 on the bottom region of valve seat 230 be opened and closed by a pressure comparable to that necessary to operate a normal larynx, or approximately 25 centimeters of water pressure.

The cylindrical housing 212 further includes a retention collar 234 in the form of a somewhat elliptical flange. The retention collar 234 is positioned between the distal end 216 of the housing 212 and the port 226. The retention collar 234 aids in maintaining the position of the device 210 in the fistula and in obtaining a seal when the voice prosthesis device is inserted through the fistula because the retention collar abuts and engages the esophageal wall 240 to retain and hold the prosthesis device in position. During insertion of the device through a fistula, the retention collar 234 snaps into position against the esophageal wall 240 when the device has been properly positioned in the patient. When in such a position, the device is firmly retained in position and is not likely to become dislodged.

The voice prosthesis device and one-way valve means mounted therein in accordance with the embodiment of FIGS. 6-7 provides a low-pressure voice prosthesis device whose operative pressure closely approximates the pressure required to operate the normal larynx of an individual and has particular application and use in conjunction with the tracheal valve disclosed in our co-pending application Ser. No. 316,055. It has been observed that the average pressure necessary to operate a normal larynx is about 35 centimeters of water and initial observation of the present invention indicates that a range of about that pressure or less readily moves the valve membrane from the closed to the open position. Such a reduction in the pressure necessary to move the one-way valve disk from the closed to the open position greatly reduces the strain upon the patient in producing alaryngeal speech and sounds similar to those produced by the patient's former larynx. Alaryngeal speech occurs when a finger covers the opening to the tracheostoma 221 and air is directed through port 226 and into the esophagus 222. Additionally, it has been found that when the one-way valve disk is in the closed position, normal swallowing by the patient will further seat the valve disk to insure an effective one-way valve in the closed position.

Also, the positioning of the one-way valve means 224 at or adjacent the distal end 216 of the housing 212 and the cooperation with the hood 225 thereon protects the valve membrane during its opening and closing excursion or movement from esophageal fluids and other matter. The hood 225 also acts as a shield which deflects esophageal fluids or swallowed matter around the housing 212 and thus prevents the downward flow of such swallowed matter from becoming impeded.

Figure 8:
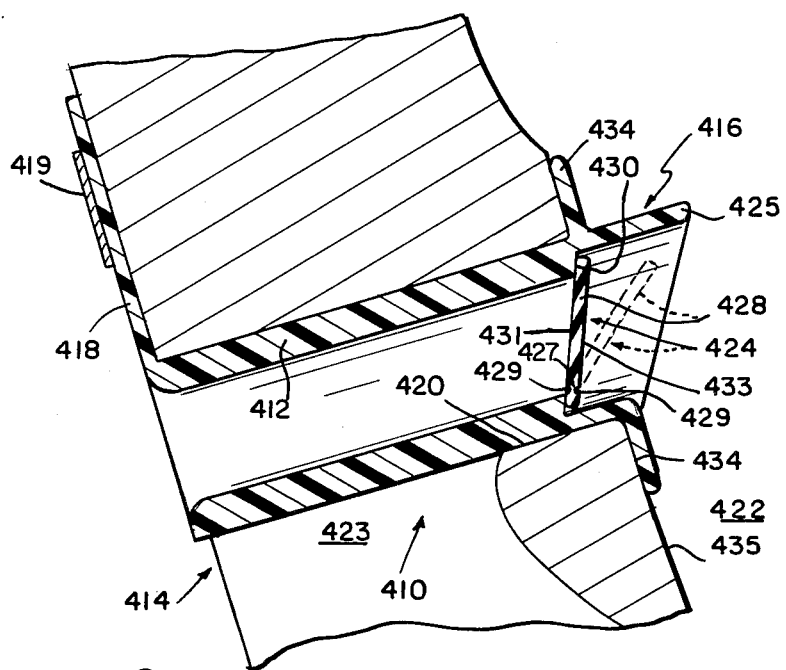
FIG. 8 illustrates a longitudinal sectional view through another one-way valve structure constructed according to the present invention.
Figure 9:
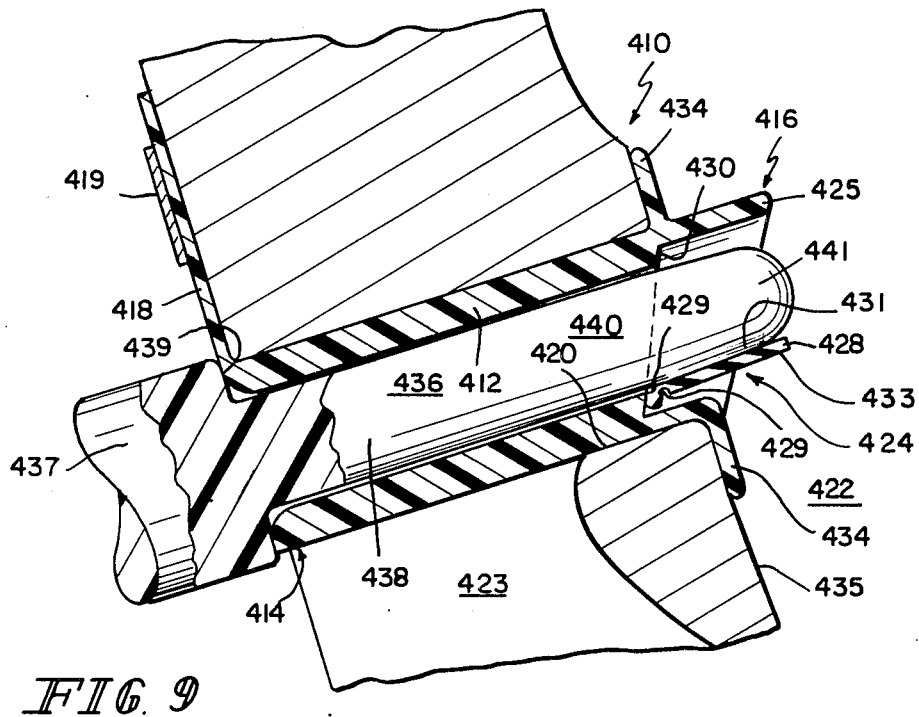
FIG. 9 illustrates a longitudinal sectional view of the valve of FIG. 8, with a tool shown in position for insertion of the valve into the wearer.

FIGS. 8-9 show another voice prosthesis device 410 in accordance with the present invention positioned in a patient having a total laryngectomy. Device 410 includes an elongated tubular housing 412 which is constructed from a biocompatible material, such as medical grade silicone, and has a proximal or tracheal end 414 and a distal or esophageal end 416. Again, the housing 412 can be right circular cylindrical in cross section, or can have other cross sectional shapes, such as right elliptical cylindrical. Mounted to the proximal end 414 are retention means in the form of a single, upwardly extending strap 418 which may be taped 419 to the neck of the wearer to assist in retaining and maintaining the voice prosthesis device 410 in a fistula 420. The elongated tubular housing 412 includes a protective hood 425 on the distal end 416 which extends into the esophagus 422. The hood 425 shields the end of the housing 412 against the influx of material flowing down the esophagus. A one-way valve 424 is positioned within and adjacent the distal end 416 of the cylindrical housing, as will hereinafter be described.

The cylindrical housing 412 in this embodiment does not include a port for expelled air from the trachea 423 to enter the tubular housing 412 of the voice prosthesis device and pass through the one-way valve 424 into the esophagus 422 to produce alaryngeal speech in the patient. The port is eliminated in this embodiment because it has been found that airflow into the open proximal end 414 of housing 412 and through one-way valve 424 is sufficient to produce alaryngeal speech. Thus, in this embodiment the open proximal end 414 serves as the port for entry of expelled air from the lungs of the wearer to enter the wearer's esophagus through one-way valve 424 and produce alaryngeal speech.

The one-way valve 424 is positioned within the tubular housing and includes an elliptical valve disk scored at 429 on both sides 431, 433 along a chord of the ellipse defined by the disk 428. The score lines 429 exend to a depth such that a very flexible region 427 of the disk 428 material remains between them. A valve seat 430 is provided at the junction of a region of the housing 412 sidewall of original thickness and a region of the housing sidewall of reduce thickness including hood 425. Seat 430 is not perpendicular to the longitudinal axis of housing 412 in this embodiment. Rather, the plane of seat 430 is inclined at an angle of approximately 70° to the longitudinal axis housing 412. It is believed that this inclination at a non-perpendicular angle to the axis of the housing 412 effects a further reduction in the pressure necessary to operate one-way valve 424. As with the embodiment of FIGS. 6-7, the disk 428 is attached to the seat 430 by the application of a small amount of a suitable adhesive between valve seat 430 and the small region of the disk 428 which is to remain stationary with respect to valve seat 430.

The cylindrical housing 412 further includes a retention collar 434 of any suitable shape. The retention collar 434 is positioned adjacent the distal end 416 of the housing 412. The retention collar 434 aids in maintaining the position of the device 410 in the fistula and in obtaining a seal when the voice prosthesis device is inserted through the fistula because the retention collar abuts and engages the esophageal side of the tracheoesophageal wall 435 to retain and hold the prosthesis device in position. During insertion of the device through a fistula, it has been observed that the retention collar snaps into position against the esophageal tissues when the device has been properly positioned in the patient. When in such a position, the device is firmly retained in position and is not likely to become dislodged.

In FIG. 9, a placement tool 436 is shown which is particularly useful in engaging the voice prosthesis device 410 for insertion of the device 410 through the fistula 420 to connect the esophagus and the tracheostoma. The placement tool 436 preferably includes an enlarged gripping or handle end 437 for holding and manipulation by the patient and a placement end 438. The placement end 438 includes a projection 440 forming with the handle 437 a shoulder 439 which is adapted to cooperate with and engage the proximal end 414 of the housing 412. When the placement tool 436 is inserted into the elongated tubular housing 412, the shoulder 439 engages proximal end 414. Additionally, the rounded, blunt end 441 provided on placement end 438 opens valve 424 to essentially the fully open position and extends to substantially the maximum projection of hood 425. This extension protects the hood 425 and valve 424 components during insertion. Additionally, the rounded nose 441 of the tool reduces the likelihood of any irritation of the sensitive tissues surrounding the fistula.

The voice prosthesis device and one-way valve means mounted therein in accordance with the embodiment of FIGS. 8-9 provides a low-pressure voice prosthesis device whose operative pressure closely approximates the pressure required to operate the normal larynx of an individual and has particular application and use in conjunction with the tracheal valve disclosed in our co-pending application Ser. No. 316,055. It has been observed that the average pressure necessary to operate a normal larynx is about 35 centimeters of water and initial observation of the present invention indicates that a range of about that pressure or less readily moves the valve membrane from the closed to the open position. Such a reduction in the pressure necessary to move the one-way valve disk 428 from the closed to the open position greatly reduces the strain upon the patient in producing alaryngeal speech and sounds similar to those produced by the patient's former larynx. Alaryngeal speech occurs when air is directed through the open proximal end 414 and into the esophagus 422. It has been found that when the one-way valve disk 428 is in the closed position, normal swallowing pressure will further seat the valve disk 428 to insure an effective one-way valve in the closed position.

Also, the positioning of the one-way valve means 424 at or adjacent the distal end 416 of the housing 412 and the cooperation with the hood 425 protects the valve disk 428 during its opening and closing excursion from esophageal fluids and other matter. The hood 425 also acts as a shield which deflects esophageal fluids or swallowed matter around the housing 412 and thus prevents the downward flow of such swallowed matter from becoming impeded.

While preferred embodiments of the voice prosthesis device and insertion tool have been shown and described above, persons skilled in the art will readily appreciate the various changes and modifications that may be made without departing from the spirit and scope of the present invention, which is defined in the following claims.

What is claimed is:

1. A voice prosthesis device for placement in a fistula in a patient to channel air from a tracheostoma to the esophagus including in combination:
   a housing having a channel extending therethrough, the housing further having a proximal end with first retaining means extending outwardly therefrom and a generally hood-like distal end,
   means for fluidly coupling the tracheostoma to the housing's channel,
   one-way valve means including a valve seat positioned within said housing, a valve membrane, means for mounting said valve membrane from said housing between said distal end and said valve seat to cooperate with said valve seat, the valve membrane having a region of reduced thickness defining a hinge, the region of the membrane on one side of the hinge being secured to the housing and the region of the membrane on the other side of the hinge being readily movable with respect to the secured region,
   second means extending outwardly from said housing for retaining the device in the fistula, said second retaining means adapted to lie against the esophagus tissue when the device has been positioned in the fistula to retain and hold the device in proper position, such that upon blocking of air flow from the tracheostoma opening, said valve membrane is moved by air passing through the fluid coupling means from a closed position against said valve seat to an open position wherein the air passing through the fluid coupling means enters the esophagus to produce alaryngeal speech by the patient.

2. The voice prosthesis device in accordance with claim 1 wherein said housing further includes a projection extending inwardly toward the center of said housing, said projection cooperating with said valve membrane to reduce the likelihood of the valve membrane overlapping said valve seat when said valve membrane is moved from said open to said closed position.

3. The voice prosthesis device in accordance with claim 1 wherein said second retention means is positioned on said housing between said port and said distal end.

4. The voice prosthesis device in accordance with claim 1 wherein about 35 centimeters of water pressure or less is sufficient to move said valve membrane from said closed to said open position and thereby permit channeled air to pass into the esophagus to produce alaryngeal speech by the patient.

5. The voice prosthesis device in accordance with claim 1 wherein said housing is comprised of a biocompatible material.

6. The voice prosthesis device in accordance with claim 1 wherein said valve seat is substantially perpendicular to the longitudinal extent of the housing in the region of the valve seat.

7. The voice prosthesis device in accordance with claim 1 wherein said valve seat makes an acute angle with the longitudinal extent of the housing in the region of the valve seat.

8. The voice prosthesis device in accordance with claim 1 wherein the means for fluidly coupling the tracheostoma to the housing's channel comprises means defining a port in a side wall of the housing, the port opening in to the tracheostoma.

9. The voice prosthesis device in accordance with claim 1 wherein the valve seat is generally annularly shaped, the valve membrane is generally disc shaped, and the region of reduced thickness extends across a portion of the valve membrane generally adjacent the region of the valve membrane which is secured to said housing.

10. The voice prosthesis device in accordance with claim 9 wherein the region of reduced thickness extends generally along a chord of the valve membrane.

11. A voice prosthesis device for placement in a fistula in a patient to channel air from a tracheostoma to the esophagus including in combination:
    a housing having a channel extending therethrough, the housing further having a proximal end and a distal end,
    means for fluidly coupling the tracheostoma to the housing's channel,
    one-way valve means including a valve seat positioned within said housing, a valve membrane, the valve membrane having a region of reduced thickness thereon defining a hinge, means for securing a region of the valve membrane on one side of the hinge to said housing to mount the valve membrane between said distal end and said valve seat, a region of the membrane on the other side of the hinge being readily movable with respect to the secured region, the valve membrane cooperating with the valve seat such that upon blockage of air flow from the tracheostoma opening, said valve membrane is moved by air passing through the fluid coupling means from a closed position against said valve seat to an open position wherein the air passing through the fluid coupling means enters the esophagus to permit the patient to produce alaryngeal speech.

12. The voice prosthesis device of claim 11 wherein said valve seat makes an acute with the longitudinal extent of the housing in the region of the valve seat.

13. The voice prosthesis device in accordance with claim 11 wherein said valve seat is substantially perpendicular to the longitudinal extent of the housing in the region of the valve seat.

14. The voice prosthesis device in accordance with claim 11 wherein about 25-35 centimeters of water pressure or less is sufficient to move said valve membrane from said closed to said open position.

15. The voice prosthesis device in accordance with claim 11 wherein the valve seat is generally annularly shaped, the valve membrane is generally disc shaped, and the region of reduced thickness extends across a portion of the valve membrane generally adjacent the region of the valve membrane secured to said housing.

16. The voice prosthesis device in accordance with claim 16 wheren said housing includes second means extending outwardly therefrom for retaining the device in the fistula, said second retaining means adapted to lie against the esophagus tissue when the device has been positioned in the fistula to retain and hold the device in proper position.

17. The voice prosthesis device in accordance with claim 16 wherein the means for fluidly coupling the tracheostoma to the housing's channel comprises the housing having a side with a port defined therein which opens into the tracheostoma.

* * * * *

UNITED STATES PATENT AND TRADEMARK OFFICE
CERTIFICATE OF CORRECTION

PATENT NO. : 4,614,516

DATED : September 30, 1986

INVENTOR(S) : Eric D. Blom and Mark I. Singer

It is certified that error appears in the above-identified patent and that said Letters Patent is hereby corrected as shown below:

At column 7, line 54, delete "reduce" and insert --reduced-- therefor;

At column 7, line 58, after "axis" insert --of--;

At column 10, line 3, delete "in to" and insert --into-- therefor;

At column 10, line 40, after "acute" insert --angle--; and

At column 10, line 57, delete "16 wheren" and insert --15 wherein-- therefor.

Signed and Sealed this

Sixth Day of January, 1987

*Attest:*

*Attesting Officer*

DONALD J. QUIGG

*Commissioner of Patents and Trademarks*